United States Patent
Chaput et al.

(10) Patent No.: US 9,192,475 B2
(45) Date of Patent: Nov. 24, 2015

(54) REINFORCED BIOCOMPATIBLE CERAMIC IMPLANT AND MANUFACTURING METHOD THEREOF

(75) Inventors: Christophe Chaput, Le Palais sur Vienne (FR); Richard Gaignon, Saint Vrain (FR); Joël Brie, Limoges (FR)

(73) Assignee: 3DCERAM, Limoges (FR)

( * ) Notice: Subject to any disclaimer, the term of this patent is extended or adjusted under 35 U.S.C. 154(b) by 154 days.

(21) Appl. No.: 13/475,151

(22) Filed: May 18, 2012

(65) Prior Publication Data

US 2012/0310365 A1 Dec. 6, 2012

(30) Foreign Application Priority Data

May 30, 2011 (FR) ...................................... 11 54724

(51) Int. Cl.
| | | |
|---|---|---|
| A61F 2/02 | (2006.01) | |
| A61F 2/28 | (2006.01) | |
| A61F 2/30 | (2006.01) | |
| A61L 27/12 | (2006.01) | |

(Continued)

(52) U.S. Cl.
CPC ........... *A61F 2/2875* (2013.01); *A61F 2/30942* (2013.01); *A61L 27/12* (2013.01); *A61L 27/56* (2013.01); *A61B 17/842* (2013.01); *A61F 2002/30011* (2013.01); *A61F 2002/3092* (2013.01); *A61F 2002/30878* (2013.01); *A61F 2002/30948* (2013.01); *A61F 2002/30952* (2013.01); *A61F 2002/30962* (2013.01); *A61F 2310/00179* (2013.01); *A61F 2310/00203* (2013.01); *A61F 2310/00293* (2013.01); *A61L 2430/02* (2013.01)

(58) Field of Classification Search
CPC ... A61F 2/3099; A61F 2/0059; A61F 2/2875; A61F 2310/00293; A61F 2002/30113; A61F 2002/30115; A61F 2002/30125; A61F 2002/30126; A61F 2002/30224; A61F 2002/30225; A61F 2002/30227; A61F 2002/30245; A61F 2002/30247
USPC ............ 623/17.17–17.19, 23.56; 606/70, 280
See application file for complete search history.

(56) References Cited

U.S. PATENT DOCUMENTS 6,238,214 B1 * 5/2001 Robinson ...................... 433/215
2006/0224242 A1 10/2006 Swords et al.

FOREIGN PATENT DOCUMENTS

| EP | 1772108 A2 | 4/2007 |
|---|---|---|
| WO | 95/07509 A1 | 3/1995 |

(Continued)

OTHER PUBLICATIONS

French Search Report dated Jan. 3, 2012, corresponding to Foreign Priority Application No. 1154724.

(Continued)

*Primary Examiner* — Elizabeth Houston
*Assistant Examiner* — Joshua Levine
(74) *Attorney, Agent, or Firm* — Young & Thompson

(57) ABSTRACT

A cranial implant designed to fill a cranial defect of the skull of a mammal or a human, wherein the cranial implant is made of biocompatible ceramic and includes an implant body having a shape and size substantially matching the shape and size of the cranial defect to be filled, wherein the implant body includes an outer face facing outside the skull and an inner face facing inside the skull when the implant disposed on the skull, characterized in that the implant includes one or more reinforcing members protruding from the inner face of the implant body. A method of manufacturing the cranial implant is also described.

13 Claims, 3 Drawing Sheets

(51) Int. Cl.
  *A61L 27/56* (2006.01)
  *A61B 17/84* (2006.01)

(56) References Cited

FOREIGN PATENT DOCUMENTS

| WO | 00/71083 | A1 | 11/2000 |
| WO | 2005/094730 | A1 | 10/2005 |
| WO | 2007/045000 | A2 | 4/2007 |
| WO | 2008106192 | A2 | 9/2008 |
| WO | 2009/129000 | A2 | 10/2009 |

OTHER PUBLICATIONS

Written Opinion dated Jan. 9, 2012, corresponding to Foreign Priority Application No. 1154724.

* cited by examiner

REINFORCED BIOCOMPATIBLE CERAMIC IMPLANT AND MANUFACTURING METHOD THEREOF

CROSS REFERENCE TO RELATED APPLICATIONS

Applicant claims priority under 35 U.S.C. 119 of French patent application no. 1154724 filed on May 30, 2011.

BACKGROUND OF THE INVENTION

The present invention relates to the field of bone implants, particularly to cranial implants designed to fill a bone defect in the skull of a human or a mammal.

Treatment of bone defects of the skull is now a major problem in maxillofacial surgery and in neurosurgery. The cranial defects may have various origins and occur especially following a developmental anomaly, a bone disease or trauma that resulted in fractures of the skull. They may also be the consequence of a neurosurgical procedure, such as a decompressive craniectomy performed in the case of post-traumatic cerebral edema, or a surgery of extraction of a brain tumor.

These bone defects are repaired during a reconstructive skull surgery, called cranioplasty, during which a bone implant destined to fill the bone defect is inserted and fixed in the skull.

The ideal material for the cranioplasty implants must be resistant, biocompatible, to eliminate the risk of inflammation, rejection and infection, and must be able to integrate with the living bone structure to ultimately form a part thereof. The integration of the implant within the native tissue proceeds via a migration process of bone cells, the osteoblasts, into the implant, which will contribute to the formation of a new bone tissue.

In this regard, several types of materials have been used to make these implants. Bone itself has thus been commonly used by performing an autograft from other bone structures of the patient, such as ribs. This solution is not without drawback: it presents risks of morbidity at the donor site; the material is only available in limited quantity and is subject to conservation challenges.

Artificial bone implants provide an interesting alternative to the use of bone grafts. In particular, metallic or plastic implants have been used. However, these implants often lack biocompatibility, and have a low osteoconductivity, which diminishes their integration ability within the existing bone tissue.

Ceramics are also advantageous materials for the manufacture of cranioplasty implants. Thus, hydroxyapatite or calcium phosphate implants are known, materials selected for their suitable biocompatibility and osteoconductivity.

WO2005/094730 A1 describes a manufacturing method of a porous ceramic cranial implant. After acquiring a three dimensional image of the skull of the patient, the bone defect is modelled by computer-aided design. Then, by rapid prototyping, an implant prototype is made, which will be used to make a calcium sulphate, resin or silicone rubber mold. Finally, the mold is used to manufacture the porous ceramic implant.

Ceramics such as hydroxyapatite or tricalcium phosphate have interesting properties for manufacturing implants. Their chemical composition, based on calcium phosphate, is close to that of the bone matter, and imparts them with a good biocompatibility. In addition, the ceramics can be manufactured porous and therefore have good osteoconductivity which allows the implants to integrate well with the bone tissue.

However, one of the drawbacks of ceramic implants is their fragility both during the manufacturing process and on the finished workpiece. Cranial implants are workpieces that frequently have a cap shape with a relatively small thickness compared to their surface. These implants are thus subjected to large internal stresses which exert in particular during the heat treatments to which the workpiece is submitted during its manufacture: debinding and sintering. They therefore lead to a distortion of the implant, which may render it unusable, since unsuited to the shape of the bone defect. They can also cause the occurence of areas of fragility of the implant likely to promote its rupture. These drawbacks make it difficult or even impossible to manufacture large size ceramic implants, which limits the use of this material to the repair of small size bone defects.

BRIEF SUMMARY OF THE INVENTION

The aim of the present invention is therefore to improve the mechanical strength of the ceramic cranial implants so as to avoid the distortion and embrittlement of the implants during their manufacture. The aim of the invention is also to improve the strength of ceramic cranial implants and to enable the manufacture of large size ceramic cranial implants.

For this purpose, the present application relates to a cranial implant designed to fill a cranial defect of the skull of a mammal or a human, wherein said cranial implant is made of biocompatible ceramic and comprises an implant body having a shape and size substantially matching the shape and size of the cranial defect to be filled, wherein the implant body comprises an outer face facing outside the skull and an inner face facing inside the skull when the implant is disposed on the skull, characterized in that the cranial implant comprises one or more reinforcing members protruding from the inner face of the implant body.

The presence of the one or more reinforcing members allows improving the mechanical strength of the implant during all the manufacturing steps of the workpiece. In particular, they can prevent distortion during debinding and sintering as well as the occurrence of embrittlement areas, such as microcracks in the implant.

The reinforcing members may consist of any protruding structure able to reinforce the mechanical strength of the implant. In particular, they may consist of reinforcing strips, or any other geometric element.

For example, the ceramic is alumina, a calcium phosphate-based ceramic, such as hydroxyapatite, tricalcium phosphate, or a mixture thereof.

The one or more reinforcing members are preferably integrally made with the body of the implant.

This design is advantageous compared to a design consisting of one or more reinforcing members laid and fixed on the body of the implant after the manufacture thereof. Besides the time savings provided by this design, the risk of poor fixation and/or disbonding of the one or more reinforcing members is also avoided, while increasing their reinforcement capacity.

Advantageously, the one or more reinforcing members protrude over a thickness smaller than the distance separating the inner face of the implant body from the outer face of the underlying anatomical structure, such as the dura mater of the mammal or the human receiving the implant, when the implant is in place on the skull.

Thus, pressure on the underlying anatomical structures is avoided, and especially on the outer face of the dura mater of the brain of the mammal or human destined to receive the implant.

In a particular embodiment, a plurality of openings are provided in at least one of the reinforcing members, wherein the openings are provided on the upper face of the one or more reinforcing members and/or on at least one side face of the one or more reinforcing members.

These openings are designed to promote debinding of the implant. Debinding consists in a heat treatment that follows the manufacture of the implant from a composition containing a polymerizable resin. Debinding is used to burn the non-polymerized resin. The openings provided in the one or more reinforcing members are designed to facilitate the release of the non-polymerized resin vapors during debinding.

Preferably, the cranial implant comprises at least two areas whose porosities are different.

For example, the implant may comprise at least one porous area and at least one non-porous area.

The one or more porous areas are designed to be colonized by the bone cells such as the osteoblasts. The pores are open and preferably interconnected, and their sizes are selected to allow a good penetration of the bone cells therein. The non-porous areas are designed to mechanically reinforce the implant.

The design of an implant exhibiting areas of different porosities is innovative compared to the prior art and requires additive-layer-manufacturing, in particular by rapid prototyping. This design is for example not possible with the molding process described in WO2005/094730 A1.

Preferably, the implant body is porous in the vicinity of part of the surface of the implant body and is non-porous at the core of the implant body.

It has indeed been noticed that, during integration of the implant within the bone tissue, the bone cells did not penetrate the entire thickness of the implant body. It is therefore advantageous to provide the porous areas only in the vicinity of the surface of the implant body, and to provide a non-porous structure at the core of the implant body which reinforces the strength of the implant.

The one or more reinforcing members are preferably non-porous, which increases their ability to mechanically reinforce the workpiece.

Several fixation modes of the implant to the skull may be considered. A possible fixation mode consists in fixing the implant by sutures.

To this end, the implant body may comprise, in the vicinity of the periphery thereof, attachment through openings.

These openings are designed to pass the suture for fixing to the bone area that surrounds the cranial defect.

The attachment openings are preferably surrounded by a non-porous attachment area, mechanically stronger than a porous area.

The reinforcing members may assume different shapes that will be selected especially depending on the shape of the implant, depending on the position of the cranial defect and depending on the underlying anatomical structures.

Thus, in one particular embodiment, the cranial implant comprises several reinforcing members of which at least a part consists of reinforcing strips and a central member, such as a ring or a circle, wherein the reinforcing strips extend star-like to the periphery of the implant from the central member.

In another embodiment, the cranial implant comprises several reinforcing members of which at least a part consists of reinforcement strips forming a grid.

The invention also relates to a method for manufacturing a biocompatible ceramic cranial implant characterized in that it comprises the following steps:

acquiring a three dimensional image of the skull of a patient having a cranial defect;

building, by computer-aided design, an implant body computer model whose shape substantially matches the cranial defect and whose size is slightly larger than the cranial defect, so as to anticipate shrinking of the ceramic during manufacturing of the cranial implant;

adding reinforcing members, by computer-aided design, to this implant body computer model, so as to obtain a cranial implant computer model, wherein the reinforcing members protrude from the inner face of the implant body;

manufacturing a biocompatible ceramic cranial implant by rapid prototyping using the cranial implant computer model.

As an exemplary rapid prototyping technique, stereolithography may be cited.

BRIEF DESCRIPTION OF THE DRAWINGS

To better illustrate the subject matter of the present invention, several embodiments will be described hereinafter, with reference to the accompanying drawings.

DETAILED DESCRIPTION OF THE INVENTION

Figure 1:
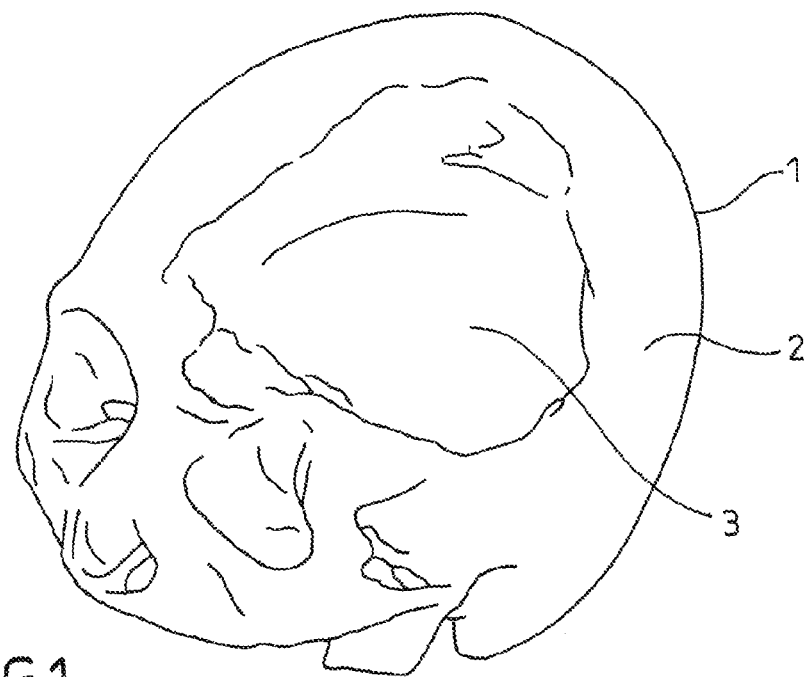
FIG. 1 shows a perspective view obtained by modeling a skull having a cranial defect.

In reference to FIG. 1, a skull 1 is shown in a perspective view. This skull has a very large cranial defect 2. The cranial defect 2 assumes the shape of a cap that covers a very large part of the frontal bone and part of the parietal bone on the left side and at the center of the skull. The defect extends frontally to the edge of the left orbit of the skull and comprises a tongue-shaped part going past the cap and going down on the left side of the left orbit. The cranial defect reveals the dura mater 3, upper membrane of the meninges, which in particular has for role to protect the brain.

Figure 2:
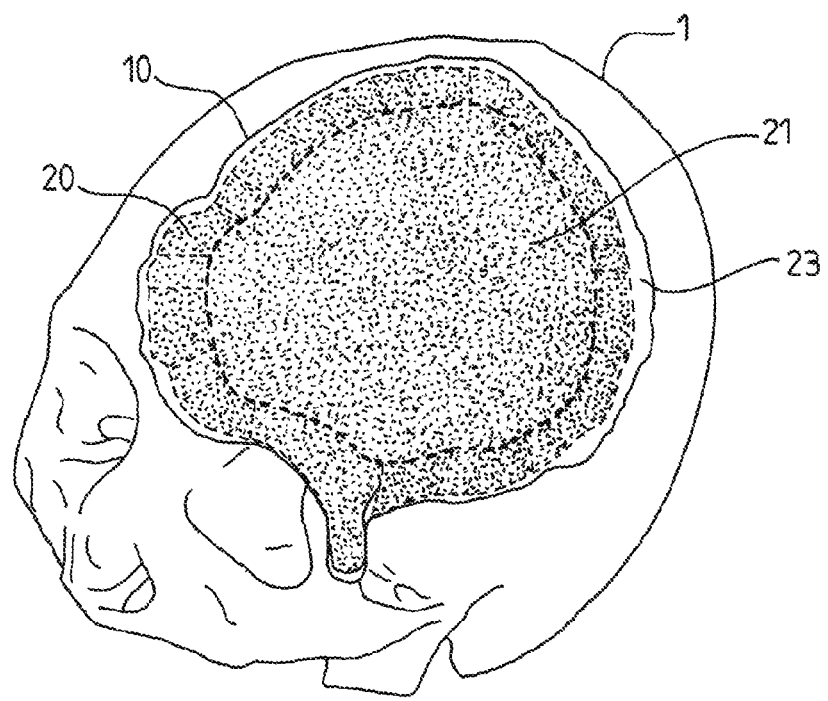
FIG. 2 shows a perspective view of the skull model shown in FIG. 1 on which is disposed a cranial implant according to a first embodiment of the invention.

FIG. 2 shows the skull of FIG. 1 bearing a cranial implant 10 according to a first embodiment of the invention. This implant comprises an implant body 20 which comprises an outer face 21 facing outside the skull and an inner face, not visible in FIG. 2 and facing inside the skull. The shape of the implant substantially reproduces the shape of the cranial defect. The implant therefore has the overall shape of a cap and has a tongue-shaped part that matches the cranial defect. The implant body 20 comprises, at the outer face 21 thereof, a supporting edge 23 that goes slightly past the cranial defect. This supporting edge 23, thinner than the rest of the implant body 20, extends over the periphery of the body of the implant, in the extension of the outer face 21 thereof and comes resting on the skull areas surrounding the cranial defect 2. This supporting edge 23 aside, the dimensions of the implant body 20 match the dimensions of the cranial defect 2, so that the implant 10 exactly fills the cranial defect.

The implant body 20 has a porous structure in the vicinity of the surface thereof. In FIG. 2, this porous structure is visible on the outer face 21 of the implant body 20. The pores are designed to promote infiltration and colonization of the implant 10 by bone cells such as osteoblasts. Their size is thus predefined and selected to let the bone cells pass. For example, the pores have a width of 500 microns. The porous structure assumes the shape of a grid with rectangular pores, but the person skilled in the art will appreciate that the porous structure of the implant body may have any other suitable shape for passage of the cells. The supporting edge 23 is non-porous, so as to provide it with a good mechanical strength. The implant 10 is fixed to the skull by sutures not shown in FIG. 2.

Figure 3:
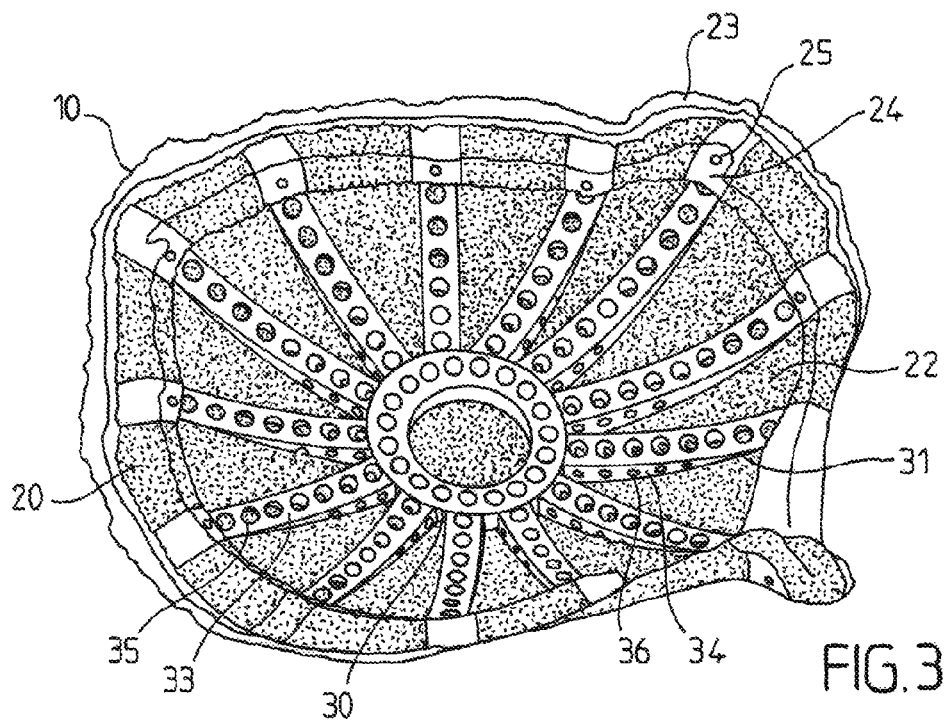
FIG. 3 shows a perspective view obtained by modeling of a cranial implant according to a first embodiment of the invention.
Figure 4:
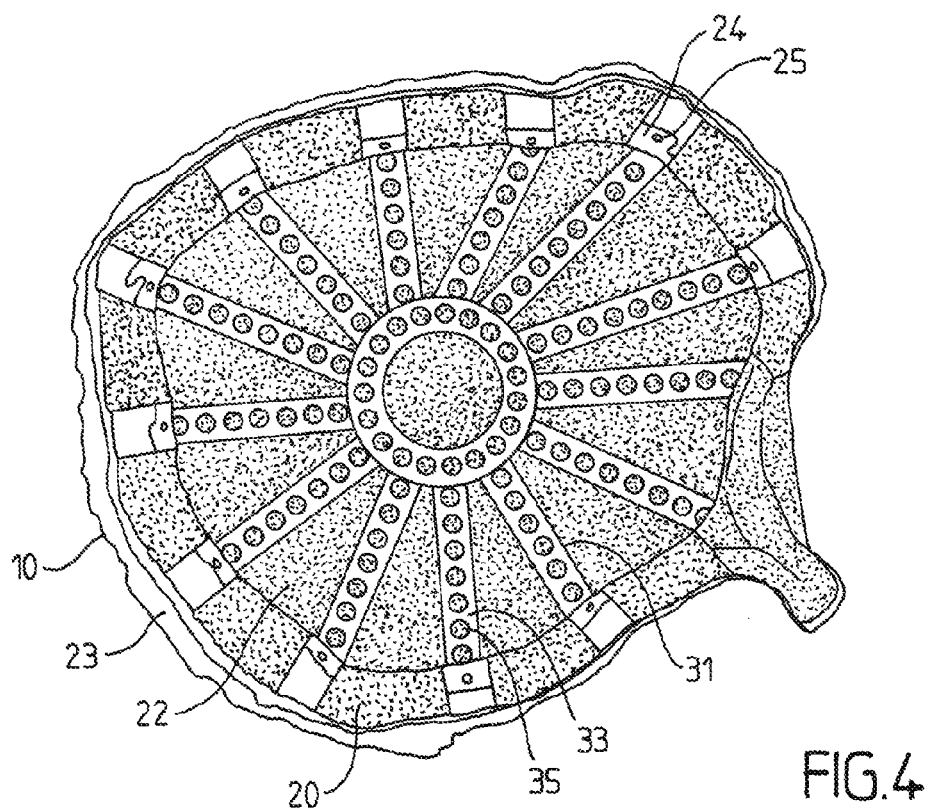
FIG. 4 shows a top view obtained by modeling of the cranial implant in FIG. 3.

In reference to FIGS. 3 and 4, a cranial implant 10 according to a first embodiment of the invention can be seen. In FIG. 3, the implant 10 is shown in perspective. The implant comprises an implant body 20 and reinforcing members 30, 31. The reinforcing members 30, 31 lay on the inner face 22 of the implant body and protrude therefrom. Herein, the reinforcing members 30, 31 assume the shape of a circular ring 30 around which reinforcement strips 31 extend in the direction of the periphery of the implant. The thickness of the reinforcing members 30, 31 is variable and is maximum at the ring 30, in the vicinity of the center of the implant 10, and reduces along the strips 31 towards the periphery of the implant 10.

Blind openings 35 are drilled in the upper face 33 of the reinforcing members 30 so as to promote debinding of the workpiece during its manufacture. They reveal the underlying inner face 22 of the implant body 20. Other openings 36, which are through openings, are drilled in the side faces 34 of the reinforcing strips 31. They are also designed to facilitate debinding. Each reinforcing strip 31 extends in the direction of the periphery of the implant to an attachment area 24 located in the vicinity of this periphery. Each attachment area 24 comprises an attachment through opening 25 designed to pass the suture required for fixing the implant 10 to the skull. In addition, a thin width supporting edge 23 surrounds the implant. As indicated above, this edge goes slightly past the contour of the defect to be filled and is designed to facilitate positioning the implant 10 on the skull areas surrounding the cranial defect.

The implant body 20 has a porous structure in the vicinity of the surface thereof. This porous structure is visible on the inner face 22 of the implant body 20. As indicated above for the outer face, this porosity has a controlled architecture and here assumes the shape of a grid with rectangular pores. While it is not visible in FIGS. 3 and 4, the implant body 20 is porous only in surface and comprises a dense structure, i.e. non-porous, core. In this manner, the bone cells can infiltrate the surface of the implant body 20 so as to promote the integration of the implant to the bone structure. In addition, the implant 10 remains strong thanks to its non-porous, core. While a major part of the surface of the implant body 20 is porous, the attachment areas 24 are designed non-porous so as not to be weakened. The reinforcing members 30, 31 and the outer edge 23 are also non-porous.

Figure 5:
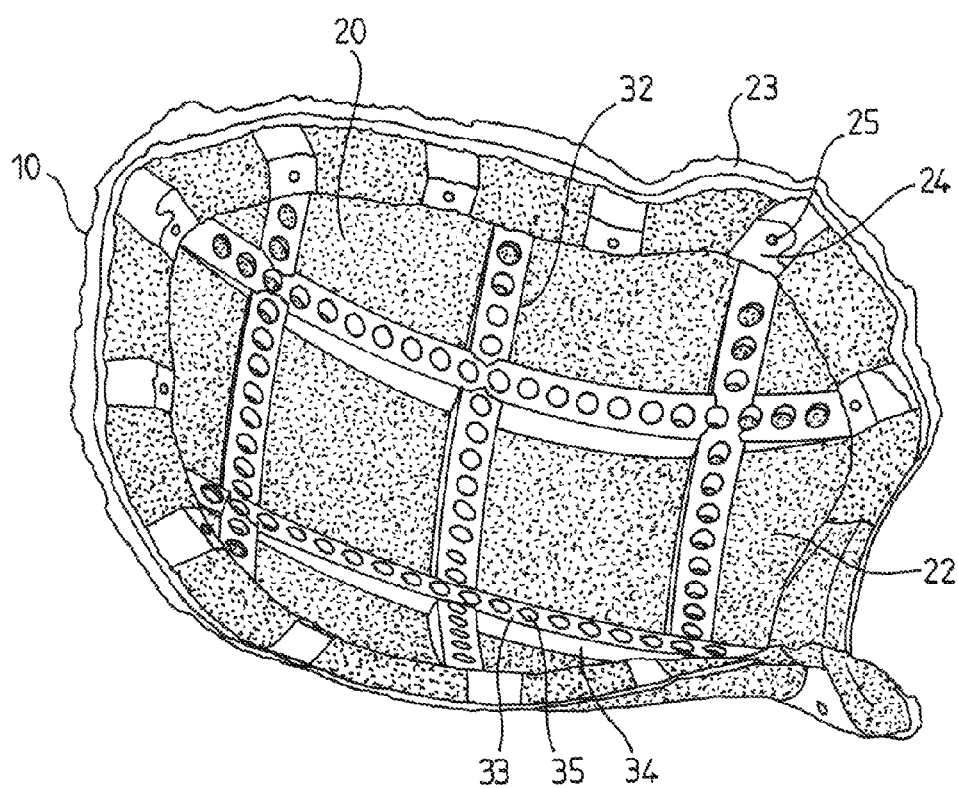
FIG. 5 shows a perspective view obtained by modeling of a cranial implant according to a second embodiment of the invention.

In reference to FIG. 5, a cranial implant 10 shown according to another embodiment of the invention can be seen. This implant 10 differs from the implant shown in FIGS. 3 and 4 by the structure of the reinforcing members 32. In FIG. 5, the reinforcing members 32 assume the shape of a grid formed by reinforcing strips 32 extending from an area adjacent to an edge of the inner face 22 of the implant body 20 to an area adjacent to another edge of the inner face 22 of the implant body 20.

We are now going to describe an exemplary method for manufacturing an implant according to the invention.

We start by acquiring an image of the skull of a patient by computerized axial tomography ("CT scan"). This image is then processed by computer-aided design (CAD) so as to build an implant body computer model. The implant being designed to fill the cranial defect, the implant body model is given a shape that matches the skull missing piece. However, in order to anticipate shrinking of the ceramic, the dimensions of the implant body model are slightly increased compared to the dimensions of the cranial defect. The shrinkage of the ceramic is a known phenomenon that occurs during sintering of ceramics and leads to shrinking of the finished workpiece compared to the green workpiece. By providing a computer model and thus a green workpiece slightly larger than the defect to be filled, a finished workpiece well fitted to the defect is obtained.

The implant body computer model may also incorporate other features such as those shown in FIGS. 3 and 4, or in FIG. 5. In particular, it may be given a specific porosity architecture, according to which the implant is porous only in the vicinity of the surface thereof and has a dense structure in the central part thereof. The porosity can assume the shape shown in FIGS. 3 to 5, i.e. a grid pattern with rectangular pores. The body implant computer model may also include a supporting edge on the peripheral contour of the implant body and designed to rest on the skull areas surrounding the cranial defect.

One or more reinforcing members are added to the implant body computer model assuming for example a star-like shape as shown in FIGS. 3 and 4, or a grid shape such as the one shown in FIG. 5. These members are preferably non-porous, and have transverse openings and lateral openings to facilitate debinding.

Generally, the thickness of the reinforcing members is selected so that the reinforcing members do not exert a pressure on the underlying dura mater when the implant is in place on the skull. The maximum thickness of the reinforcing members thus depends on the position of the cranial defect to be filled and will be determined depending on the species case by the person skilled in the art.

The reinforced implant computer model is used to manufacture a reinforced biocompatible ceramic implant by paste stereolithography, according to the method described in WO03/066326. Any other rapid prototyping process is also suitable for this manufacture.

Therefore, a paste having the following composition (in total mass %) is prepared

| | |
|---|---|
| ceramic | 80 |
| resin | 11.51 |
| photoinitiator | 0.09 |
| dispersant | 1.1 |
| plasticizer | 7.3 |

Ceramic will be for example hydroxyapatite. The resin will be an acrylate resin, such as di-ethoxylated bisphenol A dimethacrylate or 1,6-hexanediol diacrylate. The photoinitiator will be selected from photoinitiators commonly used in acrylate polymerization. Mention is made of 2,2'-dimethoxy-2-phenylacetophenone and 2-hydroxy-2-methyl-1-phenyl-propan-1-one. The dispersant is advantageously a phosphoric ester. As a plasticizer, one or more agents can be selected from the group consisting in the glycol family (e.g. polyethylene glycol), the phthalate family (e.g. dibutylphthalate), glycerol.

This paste is used to manufacture, by stereolithography, a green cranial implant such as the one shown in FIGS. 3 and 4. Manufacturing is carried out in 500 layers of 100 microns.

The green cranial implant is submitted to a heat treatment (debinding) up to 600° C. with a plateau of 2h at 600° C. and then sintering up to 1250° C. with a plateau of 1h30 at 1250° C. The finished workpiece is monolithic having a dimension of 130 mm*110 mm*40 mm. The maximum thickness of the reinforcing members 30, 31 is 5 mm, obtained at the central ring 30. The reinforcing strips 31 have a width of 6 mm, the openings 35 in the upper face 33 of the reinforcing members 30, 31 have a diameter of 3 mm, and the openings 36 in the side faces 34 of the reinforcing members have a diameter of 2 mm.

It is noted that the finished reinforced implant is not distorted compared to the implant computer model. The shape and dimensions thereof thus match those of the cranial defect that we want to fill. It does not show mechanical defects such as cracks susceptible to weaken the implant, and shows a better resistance when compared to a non-reinforced implant.

The invention claimed is:

1. A cranial implant designed to fill a cranial defect of the cranium of a mammal, said cranial implant being a monolithic structure made of biocompatible ceramic and having a shape and size substantially matching the shape and size of the cranial defect to be filled, the cranial implant comprising:
    an implant body having an outer face configured to face outside the cranium, and an inner face configured to face inside the cranium when the implant is disposed on the cranium,
        wherein the implant body is porous, the implant body having pores in the surfaces of the implant body, the pores being configured to promote infiltration and colonization of the implant by bone cells;
    one or more reinforcing members protruding from the inner face of the implant body, the reinforcing members being integrally made with the implant body and configured to protrude from the inner face over a defined thickness, wherein the reinforcing members are non-porous; and
    a plurality of attachment through-openings positioned at a periphery of the implant body, the through-openings being configured for sutures.

2. The cranial implant according to claim 1, wherein the one or more reinforcing members are configured to protrude from the inner face over a thickness smaller than the distance separating the inner face of the implant from an outer face of an underlying anatomical structure of the mammal receiving the implant, when the implant is disposed on the cranium.

3. The cranial implant according to claim 1, wherein the reinforcing members are provided with a plurality of openings, the openings being provided on an upper face of the one or more reinforcing members and/or on at least one side face of the one or more reinforcing members.

4. The cranial implant according to claim 1, wherein the implant body is porous in an outer surface portion of the implant body and is non-porous at a central core of the implant body lying underneath the surface portion.

5. The cranial implant according to claim 1, wherein the attachment through-openings are surrounded by a non-porous attachment area.

6. The cranial implant according to claim 1, wherein the cranial implant comprises several of the one or more reinforcing members comprising reinforcing strips and a central reinforcing member, wherein the reinforcing strips extend starlike to a periphery of the implant from the central member.

7. The cranial implant according to claim 1, wherein the cranial implant comprises several of the one or more reinforcing members comprising reinforcing strips forming a grid.

8. The cranial implant according to claim 6, wherein the central member forms a ring or a circle.

9. The cranial implant according to claim 1, wherein the mammal is a human.

10. The cranial implant according to claim 1, wherein the biocompatible ceramic comprises alumina, hydroxyapatite, tri-calcium phosphate, or a combination thereof.

11. The cranial implant according to claim 1, wherein the implant body further comprises a supporting edge extending around the periphery of the body, the supporting edge being non-porous and having a thickness that is thinner the thickness of the implant body.

12. The cranial implant according to claim 6, wherein the reinforcing strips have a thickness that varies, the thickness being at a maximum at the central member and the thickness reducing along the strips as the strips extend from the central member toward the periphery of the implant.

13. The cranial implant according to claim 1, wherein the implant is a monolithic structure consisting of biocompatible ceramic.

* * * * *